United States Patent
Burke et al.

(10) Patent No.: US 7,250,268 B2
(45) Date of Patent: Jul. 31, 2007

(54) ASSAY FOR MEASURING IκB KINASE ACTIVITY AND IDENTIFYING IκB KINASE MODULATORS

(75) Inventors: James R. Burke, Holland, PA (US); Shulin Wang, Monmouth Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 251 days.

(21) Appl. No.: 10/890,675

(22) Filed: Jul. 14, 2004

(65) Prior Publication Data

US 2005/0095616 A1    May 5, 2005

Related U.S. Application Data

(60) Provisional application No. 60/487,857, filed on Jul. 16, 2003.

(51) Int. Cl.
*C12Q 1/48* (2006.01)
*C12N 1/20* (2006.01)
*C12N 15/63* (2006.01)
*C12N 9/12* (2006.01)
*C12P 21/00* (2006.01)
*C12P 21/04* (2006.01)
*C07H 15/63* (2006.01)

(52) U.S. Cl. .................. 435/15; 435/252.3; 435/320.1; 435/194; 435/69.7; 435/71.1; 536/23.2

(58) Field of Classification Search ..................... None
See application file for complete search history.

(56) References Cited

OTHER PUBLICATIONS

Galye et al, Identification of regions in interleukin-1 alpha important for activity. J Biol Chem. Oct. 15, 1993;268(29):22105-11.*

Whisstock et al, Prediction of protein function from protein sequence and structure. Q Rev Biophys. Aug. 2003;36(3):307-40. Review.*

PIR_80 database Accession No. A39935 Jan. 17, 1992 Haskill et al. Alignment with SEQ ID No. 1.*

Haskill et al, Characterization of an immediate-early gene induced in adherent monocytes that encodes I kappa B-like activity. Cell. Jun. 28, 1991;65(7):1281-9.*

Whitney et al, A collaborative screening program for the discovery of inhibitors of HCV NS2/3 cis-cleaving protease activity. J Biomol Screen. Apr. 2002;7(2):149-54.*

Zamanian-Daryoush et al, NF-kappaB activation by double-stranded-RNA-activated protein kinase (PKR) is mediated through NF-kappaB-inducing kinase and IkappaB kinase. Mol Cell Biol. Feb. 2000;20(4):1278-90.*

Karin et al, Phosphorylation meets ubiquitination: the control of NF-[kappa]B activity. Annu Rev Immunol. 2000;18:621-63. Review.*

Burke, James R., "BMS-345541 Is a Highly Selective Inhibitor of IkB Kinase That Binds at an Allosteric Site of the Enzyme and Blocks NF-kB-dependent Transcription in Mice", The Journal of Biological Chemistry, vol. 278, No. 3, Issue of Jan. 17, 2003, pp. 1450-1456.

* cited by examiner

*Primary Examiner*—Sheridan Swope
(74) *Attorney, Agent, or Firm*—Brian C. Carey

(57) ABSTRACT

The present invention relates to a functional assay for IκB kinase (IKK), the proteasome and ubiquitin ligase. Cells expressing an IκB-beta-lactamase fusion protein are used to screen for inhibitors of IKK, the proteasome and ubiquitin ligase. Inhibitors identified through the inventive assay are useful in the treatment of NF-κB disorders, such as immune and inflammatory disorders. The present invention also includes cell lines useful in assays of the invention, compounds identified by assays of the invention, compositions including such compounds and methods for the treatment of disease states.

6 Claims, 20 Drawing Sheets

```
   1 ATGTTCCAGG CGGCCGAGCG CCCCCAGGAG TGGGCCATGG AGGGCCCCCG
  51 CGACGGGCTG AAGAAGGAGC GGCTACTGGA CGACCGCCAC GACAGCGGCC
 101 TGGACTCCAT GAAAGACGAG GAGTACGAGC AGATGGTCAA GGAGCTGCAG
 151 GAGATCCGCC TCGAGCCGCA GGAGGTGCCG CGCGGCTCGG AGCCCTGGAA
 201 GCAGCAGCTC ACCGAGGACG GGGACTCGTT CCTGCACTTG GCCATCATCC
 251 ATGAAGAAAA GGCACTGACC ATGGAAGTGA TCCGCCAGGT GAAGGGAGAC
 301 CTGGCTTTCC TCAACTTCCA GAACAACCTG CAGCAGACTC CACTCCACTT
 351 GGCTGTGATC ACCAACCAGC CAGAAATTGC TGAGGCACTT CTGGGAGCTG
 401 GCTGTGATCC TGAGCTCCGA GACTTTCGAG GAAATACCCC CCTACACCTT
 451 GCCTGTGAGC AGGGCTGCCT GGCCAGCGTG GGAGTCCTGA CTCAGTCCTG
 501 CACCACCCCG CACCTCCACT CCATCCTGAA GGCTACCAAC TACAATGGCC
 551 ACACGTGTCT ACACTTAGCC TCTATCCATG GCTACCTGGG CATCGTGGAG
 601 CTTTTGGTGT CCTTGGGTGC TGATGTCAAT GCTCAGGAGC CCTGTAATGG
 651 CCGGACTGCC CTTCACCTCG CAGTGGACCT GCAAAATCCT GACCTGGTGT
 701 CACTCCTGTT GAAGTGTGGG GCTGATGTCA ACAGAGTTAC CTACCAGGGC
 751 TATTCTCCCT ACCAGCTCAC CTGGGGCCGC CCAAGCACCC GGATACAGCA
 801 GCAGCTGGGC CAGCTGACAC TAGAAAACCT TCAGATGCTG CCAGAGAGTG
 851 AGGATGAGGA GAGCTATGAC ACAGAGTCAG AGTTCACGGA GTTCACAGAG
 901 GACGAGCTGC CCTATGATGA CTGTGTGTTT GGAGGCCAGC GTCTGACGTT
 951 AGGATCCATC ATGGACCCAG AAACGCTGGT GAAAGTAAAA GATGCTGAAG
1001 ATCAGTTGGG TGCACGAGTG GGTTACATCG AACTGGATCT CAACAGCGGT
1051 AAGATCCTTG AGAGTTTTCG CCCCGAAGAA CGTTTTCCAA TGATGAGCAC
1101 TTTTAAAGTT CTGCTATGTG GCGCGGTATT ATCCCGTATT GACGCCGGGC
1151 AAGAGCAACT CGGTCGCCGC ATACACTATT CTCAGAATGA CTTGGTTGAG
1201 TACTCACCAG TCACAGAAAA GCATCTTACG GATGGCATGA CAGTAAGAGA
1251 ATTATGCAGT GCTGCCATAA CCATGAGTGA TAACACTGCG GCCAACTTAC
1301 TTCTGACAAC GATCGGAGGA CCGAAGGAGC TAACCGCTTT TTTGCACAAC
1351 ATGGGGGATC ATGTAACTCG CCTTGATCGT TGGGAACCGG AGCTGAATGA
```

FIG. 3

1401 AGCCATACCA AACGACGAGC GTGACACCAC GATGCCTGTA GCAATGGCAA

1451 CAACGTTGCG CAAACTATTA ACTGGCGAAC TACTTACTCT AGCTTCCCGG

1501 CAACAATTAA TAGACTGGAT GGAGGCGGAT AAAGTTGCAG GACCACTTCT

1551 GCGCTCGGCC CTTCCGGCTG GCTGGTTTAT TGCTGATAAA TCTGGAGCCG

1601 GTGAGCGTGG GTCTCGCGGT ATCATTGCAG CACTGGGGCC AGATGGTAAG

1651 CCCTCCCGTA TCGTAGTTAT CTACACGACG GGGAGTCAGG CAACTATGGA

1701 TGAACGAAAT AGACAGATCG CTGAGATAGG TGCCTCACTG ATTAAGCATT

1751 GG (SEQ ID NO:1)

FIG. 3 cont.

1  MFQAAERPQE WAMEGPRDGL KKERLLDDRH DSGLDSMKDE EYEQMVKELQ

51  EIRLEPQEVP RGSEPWKQQL TEDGDSFLHL AIIHEEKALT MEVIRQVKGD

101  LAFLNFQNNL QQTPLHLAVI TNQPEIAEAL LGAGCDPELR DFRGNTPLHL

151  ACEQGCLASV GVLTQSCTTP HLHSILKATN YNGHTCLHLA SIHGYLGIVE

201  LLVSLGADVN AQEPCNGRTA LHLAVDLQNP DLVSLLLKCG ADVNRVTYQG

251  YSPYQLTWGR PSTRIQQQLG QLTLENLQML PESEDEESYD TESEFTEFTE

301  DELPYDDCVF GGQRLTLGSI MDPETLVKVK DAEDQLGARV GYIELDLNSG

351  KILESFRPEE RFPMMSTFKV LLCGAVLSRI DAGQEQLGRR IHYSQNDLVE

401  YSPVTEKHLT DGMTVRELCS AAITMSDNTA ANLLLTTIGG PKELTAFLHN

451  MGDHVTRLDR WEPELNEAIP NDERDTTMPV AMATTLRKLL TGELLTLASR

501  QQLIDWMEAD KVAGPLLRSA LPAGWFIADK SGAGERGSRG IIAALGPDGK

551  PSRIVVIYTT GSQATMDERN RQIAEIGASL IKHW (SEQ ID NO:2)

FIG. 4

| T | B | T | B | T | B | T | B | T | B | T | B | T |
|---|---|---|---|---|---|---|---|---|---|---|---|---|
| B | T | B | T | B | T | B | T | B | T | B | T | B |
| T | B | T | B | T | B | T | B | T | B | T | B | T |
| B | T | B | T | B | T | B | T | B | T | B | T | B |
| T | B | T | B | T | B | T | B | T | B | T | B | T |
| B | T | B | T | B | T | B | T | B | T | B | T | B |
| T | B | T | B | T | B | T | B | T | B | T | B | T |
| B | T | B | T | B | T | B | T | B | T | B | T | B |
| T | B | T | B | T | B | T | B | T | B | T | B | T |

FIG. 18

FIG. 18 shows the "checkerboard" pattern of alternating stimulated (T, total) and unstimulated (B, blank) samples used to analyze the well-to-well variability across an entire 384-well plate.

ASSAY FOR MEASURING IκB KINASE ACTIVITY AND IDENTIFYING IκB KINASE MODULATORS

CROSS-REFERENCE TO RELATED APPLICATION

This application claims priority to U.S. Provisional Patent Application No. 60/487,857, filed Jul. 16, 2003.

FIELD OF THE INVENTION

The present invention relates to a functional assay for IκB kinase (IKK), the proteasome and ubiquitin ligase. Cells expressing an IκB-beta-lactamase fusion protein are used to screen for inhibitors of IKK, the proteasome and ubiquitin ligase. Inhibitors identified through the inventive assay are useful in the treatment of NF-κB disorders, including inflammatory disorders.

BACKGROUND OF RELATED TECHNOLOGY

The nuclear transcription factor NF-κB is a key mediator of the inflammatory response to cytokines such as TNFα and IL-1 by acting as a transcriptional activator of downstream proinflammatory genes. The N-terminal region of the NF-κB protein has a Rel-homology domain (RHD) that allows the protein to bind DNA, and also contains a nuclear localization sequence. In unstimulated cells, the NF-κB heterodimer is normally not found in the nucleus, it is sequestered in the cytosol by IκB, an inhibitor of κB that blocks the nuclear localization signal of NF-κB.

The dormant form of NF-κB can be quickly activated by a large number of extracellular signals, including mitogens, cytokines (such as TNFα and IL-1), viral proteins, antigens, phosphatase inhibitors and ultraviolet light. Binding of proinflammatory cytokines, for example, to their receptors results in the activation of IκB kinase (IKK) which then phosphorylates IκB on specific serine residues. This phosphorylation of IκB results in the rapid degradation of IκB by the ubiquitin-proteasome pathway. Once IκB is removed, NF-κB is free to translocated into the nucleus of the cell and transcriptionally activate its targeted genes.

The ubiquitin-proteasome pathway involves the covalent conjugation of cellular proteins with the small polypeptide ubiquitin. Thereafter, the conjugated proteins are hydrolyzed by a 26S proteolytic complex containing a 20S degradative particle called the proteasome. This multicomponent system is known to catalyze the selective degradation of highly abnormal proteins and short-lived regulatory proteins, such as IκB.

Therefore, IKK, the proteasome and ubiquitin represent important regulatory steps in the inflammatory response and are attractive targets for therapeutic intervention. Accordingly, there is a need to develop assays which permit the study of agents which may affect the activity of IKK, the proteasome and ubiquitin. Agents found to be useful for affecting the activity of IKK, the proteasome and ubiquitin are potentially valuable therapeutic agents for the treatment of NFκB-mediated diseases.

SUMMARY OF THE INVENTION

The present invention relates to a functional assay for IκB kinase (IKK), the proteasome and ubiquitin ligase. Cells expressing an IκB-beta-lactamase fusion protein are used to screen for inhibitors of IKK, the proteasome and ubiquitin ligase. Inhibitors identified through the inventive assay are useful in the treatment of NFκB-mediated disorders, such as inflammatory disorders.

In one aspect, the present invention is directed to an assay for identifying a compound that inhibits IKK activity, comprising the steps of: (a) providing a cell which expresses a fusion protein which comprises IκB and a reporter protein; (b) contacting the cell with a test compound; and (c) determining whether the test compound inhibits IKK activity. The assay is desirably a cell-based assay and may be conducted in a high throughput manner. The cell desirably has ATTC Deposit Number PTA-4852, and the fusion protein may be encoded by a nucleic acid molecule comprising the nucleic acid sequence set forth in SEQ ID NO:1 and may comprise the amino acid sequence set forth in SEQ ID NO:2. The reporter protein may be beta-lactamase, and the step of determining whether said test compound inhibits IKK activity may be determined by measuring the expression of beta-lactamase.

In another aspect, the present invention is directed to a compound identified by an assay of the present invention.

In another aspect, the present invention is directed to a composition comprising a compound identified by an assay of the present invention.

In another aspect, the present invention is directed to a method of treating a patient suffering from a disease mediated by NF-κB by administering to the patient a therapeutically effective amount of a compound identified by an assay of the present invention.

In another aspect, the present invention is directed to an assay for identifying a compound that inhibits proteasome activity, comprising the steps of: (a) providing a cell which expresses a fusion protein comprising IκB and a reporter protein; (b) contacting the cell with a test compound; and (c) determining whether the test compound inhibits proteasome activity.

In another aspect, the present invention is directed to an assay for identifying a compound that modulates NF-κB activity, comprising the steps of: (a) providing a cell which expresses a fusion protein comprising IκB and a reporter protein; (b) contacting the cell with a test compound; and (c) determining whether the test compound modulates NF-κB activity.

In another aspect, the present invention is directed to an assay for identifying a compound that inhibits ubiquitin ligase activity, comprising the steps of: (a) providing a cell which expresses a fusion protein comprising IκB and a reporter protein; (b) contacting the cell with a test compound; and (c) determining whether the test compound inhibits ubiquitin ligase activity.

In another aspect, the present invention is directed to a cell having ATCC Deposit Number PTA-4852.

In another aspect, the present invention is directed to a nucleic acid molecule comprising the nucleic acid sequence set forth in SEQ ID NO:1.

In another aspect, the present invention is directed to a nucleic acid molecule encoding a polypeptide comprising the amino acid sequence set forth in SEQ ID NO:2.

In another aspect, the present invention is directed to a cell comprising a nucleic acid molecule comprising the nucleic acid sequence set forth in SEQ ID NO:1 or a cell expressing a polypeptide comprising the amino acid sequence set forth in SEQ ID NO: 2.

In another aspect, the present invention is directed to an assay for identifying a compound that inhibits IKK activity, comprising the steps of: (a) providing a cell comprising a nucleic acid molecule comprising the nucleic acid sequence set forth in SEQ ID NO:1 or a cell expressing a polypeptide comprising the amino acid sequence set forth in SEQ ID NO:2; (b) contacting the cell with a test compound; and (c) determining whether the test compound inhibits IKK activity.

BRIEF DESCRIPTION OF THE DRAWINGS

FIG. 3 shows the nucleic acid sequence encoding the pIκB-BLA construct.

FIG. 4 shows the polypeptide sequence of the pIκB-BLA construct.

FIG. 14B shows the effect of TNFα treatement followed by loading with CCF4/AM at various times.

FIG. 18 shows an analysis of well-to-well variability across an entire 384-well plate.

DETAILED DESCRIPTION OF THE INVENTION

Figure 1:
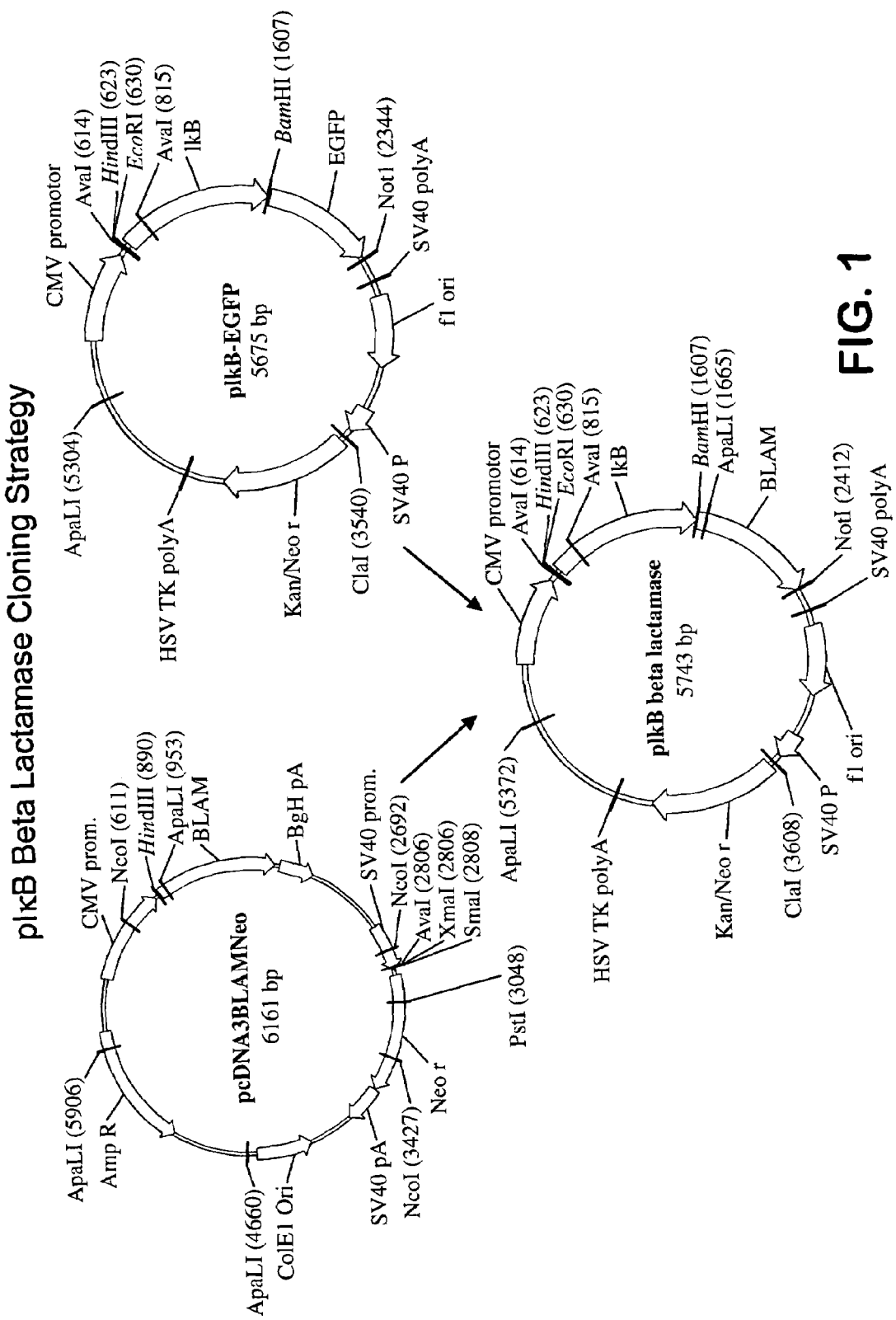
FIG. 1 is a schematic diagram of the IκB-BLA vector construction.

The present invention is directed to a functional assay for IκB kinase (IKK), the proteasome and ubiquitin ligase, such as by measuring the signal-regulated degradation of IκB. As IKK phosphorylates IκB, resulting in the degradation of IκB, assays involving the measurement of IκB degradation permit the study of agents for their ability to modulate IKK activity. Furthermore, as IKK-mediated phosphorylation of IκB is required for and followed by ubiquitination of IκB, which is required for and followed by proteasome-dependent degradation of IκB, assays of the present invention are useful for the study of proteasome and ubiquitin ligase inhibitors as well. The therapeutic utility of inhibitors of ubiquitin ligase is expected to be the same as that of IKK inhibitors.

As shown in the working Examples below, in the present invention an IκBα-beta-lactamase (IκBα-Bla) fusion protein construct (N-terminal IκBα and C-terminal Bla) ("fusion construct") has been made and utilized. The IκB-Bla fusion protein ("fusion protein") is phosphorylated and degraded in a manner similar to IκB alone, and is therefore useful for the study of IKK, the proteasome and ubiquitin ligase in assays of the present invention. The entire fusion protein was found to degrade intact, an important characteristic necessary to ensure that β-lactamase activity accurately reflects IκB levels. The ability of the fusion protein to be degraded intact was verified using in vitro synthesized IκB-Bla and cell lysates that contain a functional ubiquitin-proteasome pathway.

Once the fusion construct was characterized, Jurkat cells were transfected with the IκB-Bla reporter constructs (pIκB-BLA) and stable transfectants were selected. Flow cytometry was used to select populations of cells expressing various levels of the reporter. This sampling of varying reporter expression levels ensured that a cell line was isolated with sufficient expression for high throughput screening (HTS) but with correct regulation of the NFκB pathway. The resulting clonal cell lines were tested for reporter levels upon stimulation of the NFκB pathway, by treating the cells with TNFα and monitoring the steady state levels of IκB-Bla using CCF2/AM.

Controls were important to demonstrate specificity and confirm mode of action. To demonstrate that the degradation of the IκB-Bla reporter was due to IKK activity, a control reporter construct was made wherein the residues in IκBα that are phosphorylated by IKK were mutated to alanine (S32A, S36A). In addition to this mutant construct, proteasome inhibitors such as MG132 and lactacystin were used to verify that the IKK-mediated degradation of the reporter was via the ubiquitin-proteasome pathway. Finally, the degradation kinetics of the IκB-Bla reporter were compared to that of endogenous IκBA, determined by western blot.

As set forth below, in the present invention an IκBα-Bla fusion protein construct has been made having a nucleic acid sequence having 1752 base pairs, as shown in FIG. 3 (SEQ ID NO:1) and a polypeptide sequence having 584 amino acid residues, as shown in FIG. 4 (SEQ ID NO:2). One skilled in the art, however, will recognize that derivatives and homologues of the inventive IκBα-Bla fusion protein construct may be used in the present invention. For example, nucleic acid sequences encoding the IκBα-Bla fusion protein construct may be altered by substitutions, additions, or deletions that provide for functionally equivalent-conservative variants of the IκBα-Bla fusion protein construct. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

Other conservative amino acid substitutions can be taken from Table 1, below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, D-Ile, Leu, D-Leu, Val, D-Val |
| Phenylalanine | F | D-Phe, Tyr, D-Thr, L-Dopa, His, D-His, Trp, D-Trp, Trans-3, 4, or 5-phenyl-proline, cis-3,4, or 5-phenyl-proline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein stability; such analogs may contain, for example, one or more non-peptide bonds (which replace the peptide bonds) in the protein sequence. Also included are analogs that include residues other than naturally occurring L-amino acids, e.g., D-amino acids or non-naturally occurring or synthetic amino acids, e.g., β or γ amino acids.

The IκBα-Bla fusion protein construct used in the present invention may be modified by, for example, phosphorylation, sulfation, acylation, or other protein modifications. It may also be modified with a label capable of providing a detectable signal, either directly or indirectly, including, but not limited to, radioisotopes and fluorescent compounds.

Further, modulators found to affect IKK, proteasome and ubiquitin ligase activity may be introduced into an animal model in order to study the ability of such modulators in vivo.

Drug screening assays are also provided in the present invention. By using assays of the present invention, one skilled in the art can use these to screen for drugs which are either agonists or antagonists of the normal cellular function or their role in cellular signaling.

In one aspect, assays of the present invention evaluate the ability of a compound to modulate IKK, proteasome or ubiquitin ligase activity. The term "modulating" encompasses enhancement, diminishment, activation or inactivation of IKK, proteasome or ubiquitin ligase activity.

"IKK-associated disorders", "Proteasome-associated disorders", "Ubiquitin-ligase associated disorders" and "NF-κB-associated disorders" refer to any disorder or disease state in which IKK, proteasome, ubiquitin ligase or NF-κB, respectively, plays a regulatory role in the metabolic pathway of that disorder or disease. Such disorders or diseases include, but are not limited to, immune and inflammatory disorders and cancer. As used herein the term "treating" refers to the alleviation of symptoms of a particular disorder in a patient, the improvement of an ascertainable measurement associated with a particular disorder, or the prevention of a particular immune, inflammatory or cellular response.

A compound which acts as an IKK, proteasome or ubiquitin ligase modulator may be administered for therapeutic use as a raw chemical or may be the active ingredient in a pharmaceutical formulation. Such formulations of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Compounds of the present invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

Such compounds may, for example, be administered in a form suitable for immediate release or extended release. Immediate release or extended release may be achieved by the use of suitable pharmaceutical compositions comprising compounds of the present invention, or, particularly in the case of extended release, by the use of devices such as subcutaneous implants or osmotic pumps. Compounds of the present invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art.

Compounds of the present invention may also be delivered through the oral cavity by sublingual and/or buccal administration. Molded tablets, compressed tablets or freeze-dried tablets are exemplary forms which may be used. Exemplary compositions include those formulating the compound(s) of the present invention with fast dissolving diluents such as mannitol, lactose, sucrose and/or cyclodextrins.

Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IKK-associated disorders, Proteasome-associated disorders, Ubiquitin ligase-associated disorders and NF-κB-associated disorders.

The compounds of the present invention may be employed alone or in combination with each other and/or other suitable therapeutic agents useful in the treatment of IKK-associated disorders, Proteasome-associated disorders, Ubiquitin ligase-associated disorders and NF-κB-associated disorders.

In another aspect, the present invention relates to the use of an isolated nucleic acid in "antisense" therapy. As used herein, "antisense" therapy refers to administration or in situ generation of oligonucleotides or their derivatives which specifically hybridize under cellular conditions with the cellular mRNA and/or genomic DNA encoding IKK, the proteasome or ubiquitin ligase of the present invention so as to inhibit expression of the encoded protein, e.g., by inhibiting transcription and/or translation. In general, "antisense" therapy refers to the range of techniques generally employed in the art, and includes any therapy which relies on specific binding to oligonucleotide sequences.

Gene constructs useful in antisense therapy may be administered may be administered in any biologically effective carrier, e.g., any formulation or composition capable of effectively delivering a nucleic acid sequence to cells in vivo. Approaches include insertion of the subject gene in viral vectors including recombinant retroviruses, adenoviruses, adeno-associated viruses, and herpes simplex virus-1, or recombinant bacterial or eukaryotic plasmids. Viral vectors transfect cells directly; an advantage of infection of cells with a viral vector is that a large proportion of the targeted cells can receive the nucleic acid. Several viral delivery systems are known in the art and can be utilized by one practicing the present invention.

In addition to viral transfer methods, non-viral methods may also be employed. Most non-viral methods of gene transfer rely on normal mechanisms used by mammalian cells for the uptake and intracellular transport of macromolecules. Exemplary gene delivery systems of this type include liposomal derived systems, poly-lysine conjugates, and artificial viral envelopes. Nucleic acid sequences may also be introduced to cell(s) by direct injection of the gene construct or by electroporation.

In clinical settings, the gene delivery systems can be introduced into a patient by any of a number of methods, each of which is known in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells which produce the gene delivery system.

The following section sets forth materials and methods used in the present invention, and which were utilized in the Examples set forth hereinbelow.

Materials and Methods

A. pIκB-BLA Vector Construction.

Expression vector pIκB-EGFP (Clontech Laboratories, Palo Alto, Calif.) was digested with BamH1 and Not1 restriction enzymes to remove the EGFP-encoding DNA fragment. The beta-lactamase (BLAM) cDNA fragment was generated by PCR using a 5' BamH1 encoding primer and a 3' Not1 encoding primer and pcDNA3BLAMNeo (Aurora Biosciences, San Diego, Calif.) as the template. The BLAM PCR fragment was digested with BamH1 and Not1 and subsequently inserted into the BamH1/Not1 digested pIκB-EGFP vector above to create the pIκB beta-lactamase expression vector (pIκB-BLA), shown in FIG. 1.

B. Subculture Protocol for Jurkat pIκB-BLA Cells.

Culture Media:
RPMI-containing HEPES and L-glutamine (Gibco BRL, Cat. # 22400-071)
10% FBS (Gibco BRL Cat. # 16140-071)
1× PenStrep (Gibco BRL Cat. # 15140-122)
Optional: G418 800 μg/ml (Gibco Cat. # 10131-027)
OPTI-MEM 1 reduced Serum Medium (Gibco BRL, Cat. # 11058-021) plus 0.5%
FBS (Charcoal/Dextran treated, Gibco BRL, Cat. # SH30068.03)
1. Cells were kept at density between 200,000 to 1,000,000/ml. Fed every two days with RPMI/10% FBS and incubated at 37° C., 5% $CO_2$ and 90% humidity.
2. Cells were fed by centrifuging for 5 min. at 1000 rpm. Media was aspirated and cells were resuspended in RPMI/10% FBS by pipetting up and down a few times. Cells were transferred to new flasks.

C. Standard Assay Protocol for Jurkat pIκB-BLA in 384-well Plate.

1. Changed to New Media (RPMI/10% FBS) the day before the assay.
   a. Harvested the cells and resuspended in OPTI-MEM with 0.5% CD FBS at a density of 1,500,000 cells/ml.
   b. Dispensed 20 μl of cells per well in 384-well, clear bottom assay plate (Greiner 384-well plate Cat # N5-8102, Greiner 384 lids, Cat # N2-9139).
   c. Incubated the cells at 37° C., 5% $CO_2$ and 90% humidity for 1 hour.
   d. Added 20 μl OPTI-MEM/0.5% CD FBS with 20 ng/ml TNF-α (R&D Systems, Cat. # 210-TA).
   e. Kept the plate in 37° C., 5% $CO_2$ and 90% humidity for 1 hour.
   f. Added 8 μl of 18×CCF4-AM Staining Solution for 2 hours in the dark with gentle shaking at RT.

18×CCF4-AM Staining Solution:
   a. Added 18 μl of CCF4/AM (1 mM) to 60 μl of Sol B
   b. Vortexed to mix
   c. Added 1 ml of Sol C
   d. Vortexed to mix Note: This 18× stock resulted in 3 μM final concentration of CCF4; scaled down amount of CCF4/AM for lower concentrations while maintaining the same concentration of Solutions B and C.
CCF4/AM loading kit (CCF4/AM, solutions B and C, DMSO): ABSC product # 00 100 042
5 mg CCF4/AM: ABSC product # 00 100 112
Sol B, Sol C, DMSO: ABSC product # 00 100 156
   a. Assay plates were read on the LJL Analyst using the following filter settings: a) 405/20 nm excitation and 460/50 nm emission (scan #1), and b) 405/20 nm excitation and 530/25 nm emission (scan #2).

Instrument Settings:
Microplate format settings for Greiner 384-wells plates: used preset Greiner square flat 384 setting.
Used z-height setting of 2 mm.
Detector settings: Smart Read Plus detector counting with sensitivity setting of 1, read time of 100,000 μs and attenuator of medium.
A 50/50 beam splitter in the bottom-read setup was used for both scans.
Report setting: Raw data, Subtracted data and ratio 1/2
   a. Raw emission values were automatically subtracted from a media-only blank containing CCF4/AM staining solution in cell culture media (no cells). The ratios of 460 nm/530 were calculated by the LJL Analyst.

EXAMPLE 1

IκBα-Bla Fusion Protein Wild-Type and Mutant Constructs

Figure 2:
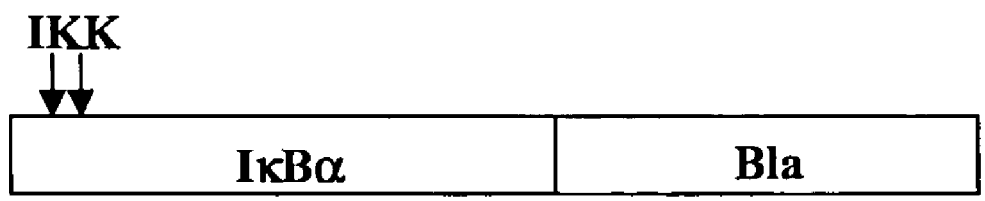
FIG. 2 shows a schematic diagram of the pIκB-BLA construct.

An IκBα-Bla fusion protein construct (pIκB-BLA; N-terminal IκBα and C-terminal Bla) was made as set forth in Section A of Materials and Methods and served as the starting point for assay development. The pIκB-BLA construct is shown schematically in FIG. 2 and has a nucleic acid sequence comprising 1752 base pairs, as shown in FIG. 3 (SEQ ID NO:1) and a polypeptide sequence comprising 584 amino acid residues, as shown in FIG. 4 (SEQ ID NO:2).

As IKK is known to phosphorylate IκB on serines-32 and -36 (indicated respectively by arrows in FIG. 2), serine-to-alanine mutants (S32A, S36A) were created as a control for phosphorylation-induced degradation of the fusion reporter.

EXAMPLE 2

Transfection of Protein Constructs and Cell Selection

Figure 5:
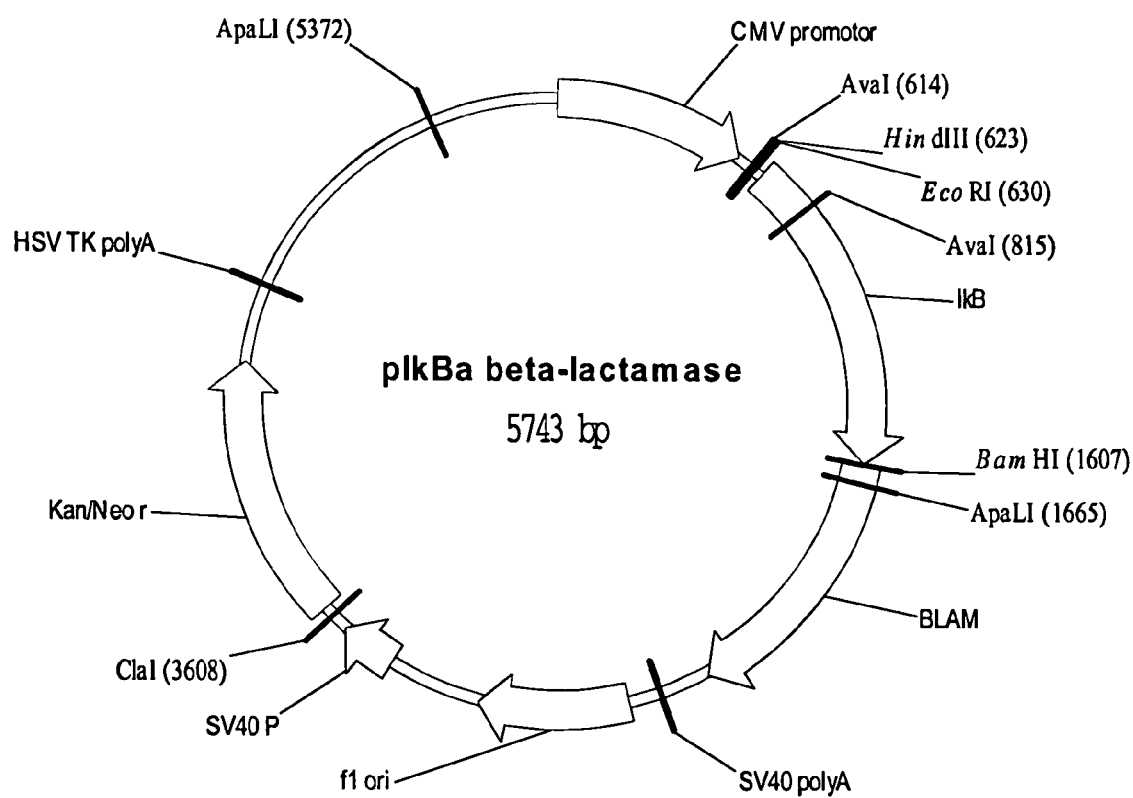
FIG. 5 shows a vector MAP of the pIκB-BLA construct.

The wild-type and S32A, S36A mutant constructs in pIκB-BLA vector (MAP shown in FIG. 5) were introduced into Jurkat cells by transfection and G418-resistant cells were selected. The stable transfectants were loaded with CCF2/AM and sorted for β-lactamase levels using flow cytometry. Two populations of cells were sorted, as shown in FIG. 6, representing high (R1; upper left) and moderate (R2) levels of β-lactamase activity.

Assays involving a decrease in β-lactamase activity upon stimulus treatment have shown that simply selecting the cells with the highest reporter levels often leads to non-responsive or less-responsive clones. Consistent with this, it was found in the present invention that cells derived from the R1 high β-lactamase region of FIG. 6 showed less robust response to TNFα treatment than cells from the R2 region of FIG. 6 (data not shown). FIG. 7 shows the response to TNFα for four representative clonal lines derived from cells sorted from the R2 region of FIG. 6. The cells were treated with 10 ng/ml TNFα for 30 minutes at 37° C. and then loaded with 1 μM CCF2/AM for 1 hour at room temperature. β-lactamase levels were determined using a LJL Analyst fluorescence plate reader and are expressed as a 460/530 ratio where high ratios correspond to high β-lactamase activity.

Figure 6:
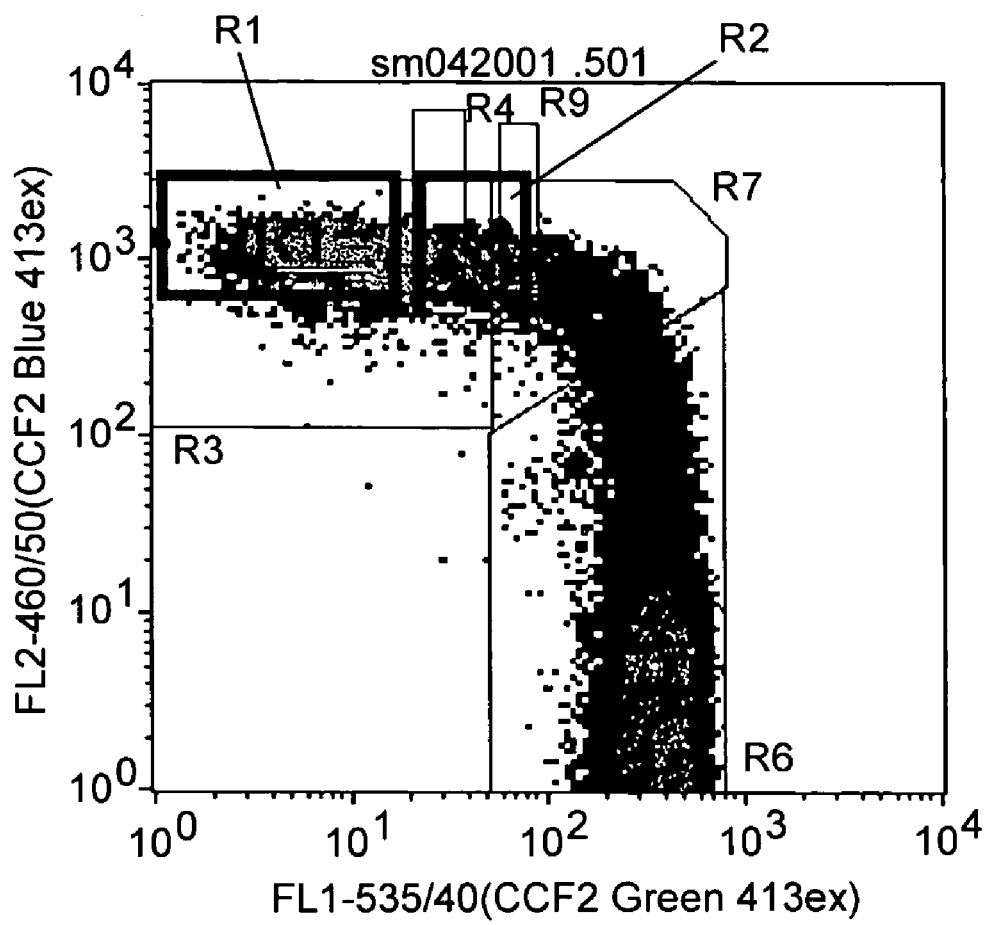
FIG. 6 shows β-lactamase activity in two populations of sorted cells; high (R1) and moderate (R2).
Figure 7:
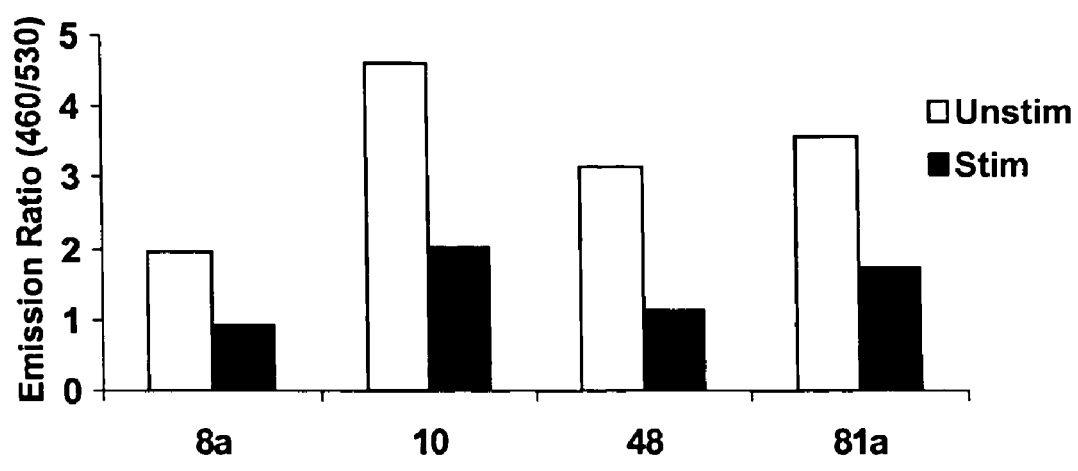
FIG. 7 shows the response to TNFα for four representative clonal lines derived from cells sorted from the R2 region shown in FIG. 6.

The observed response of the clones shown was approximately equal to the response of a pool of cells sorted from the R2 region of FIG. 6, demonstrating that the individual clonal lines are representative of the responding population.

For the remaining analyses, the 81a cell line was used as it gave the most robust and reproducible response.

The 81a cell line is a Human T-Cell (Jurkat) designated 81a/IκB-BLA and was deposited with the American Type Culture Collection ("ATCC") as Deposit Number PTA-4852 on Dec. 10, 2002. The ATCC is located at 10801 University Boulevard, Manassas, Va. 20110-2209, USA. The ATCC deposit made in the present invention was made pursuant to the terms of the Budapest Treaty on the international recognition of the deposit of microorganisms for purposes of patent procedure.

EXAMPLE 3

Responsiveness of Cells Transfected with Wild-Type Construct

Figure 8A:
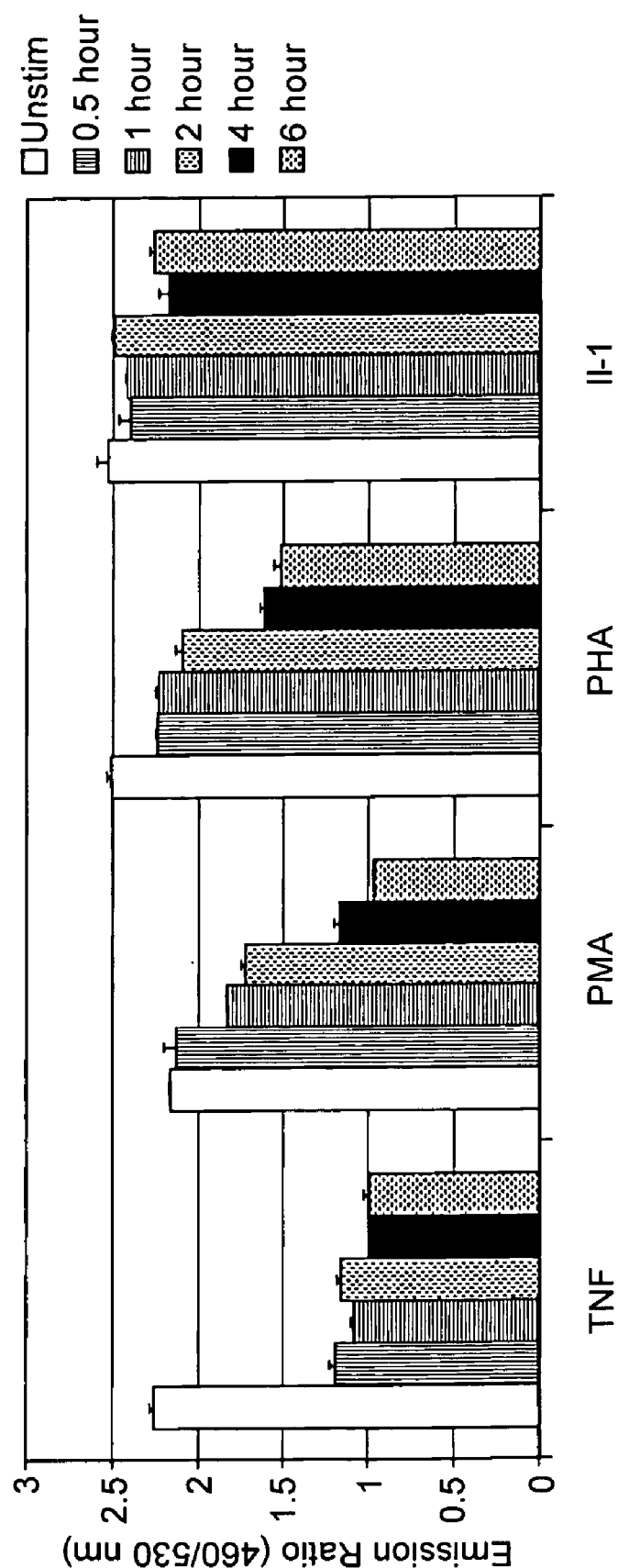
FIG. 8A shows the responsiveness of Jurkat IκB-Bla cells to proinflammatory treatments known to activate the NFκB pathway.

The responsiveness of the Jurkat IκB-Bla cells to proinflammatory treatments known to activate the NFκB pathway was tested. Cells were treated with 10 ng/ml TNFα, 10 nM PMA, 10 μg/ml PHA or 100 ng/ml IL-1β for the times indicated in FIG. 8A and then loaded with CCF2 and read on a fluorescence plate reader. As shown in FIG. 8A, the cell line was able to respond to TNFα, phorbol ester (PMA) and phytohemaglutinin (PHA) by decreasing the level of IκB-Bla reporter. TNFα showed the most robust response, with a reproducible 2-fold decrease in β-lactamase activity achieved within 30 minutes. A similar magnitude of decrease in β-lactamase activity was obtained with extended treatment with PMA or PHA. The apparent insensitivity to IL-1β may be explained by low expression of IL-1 receptor in Jurkat cells.

Figure 8B:
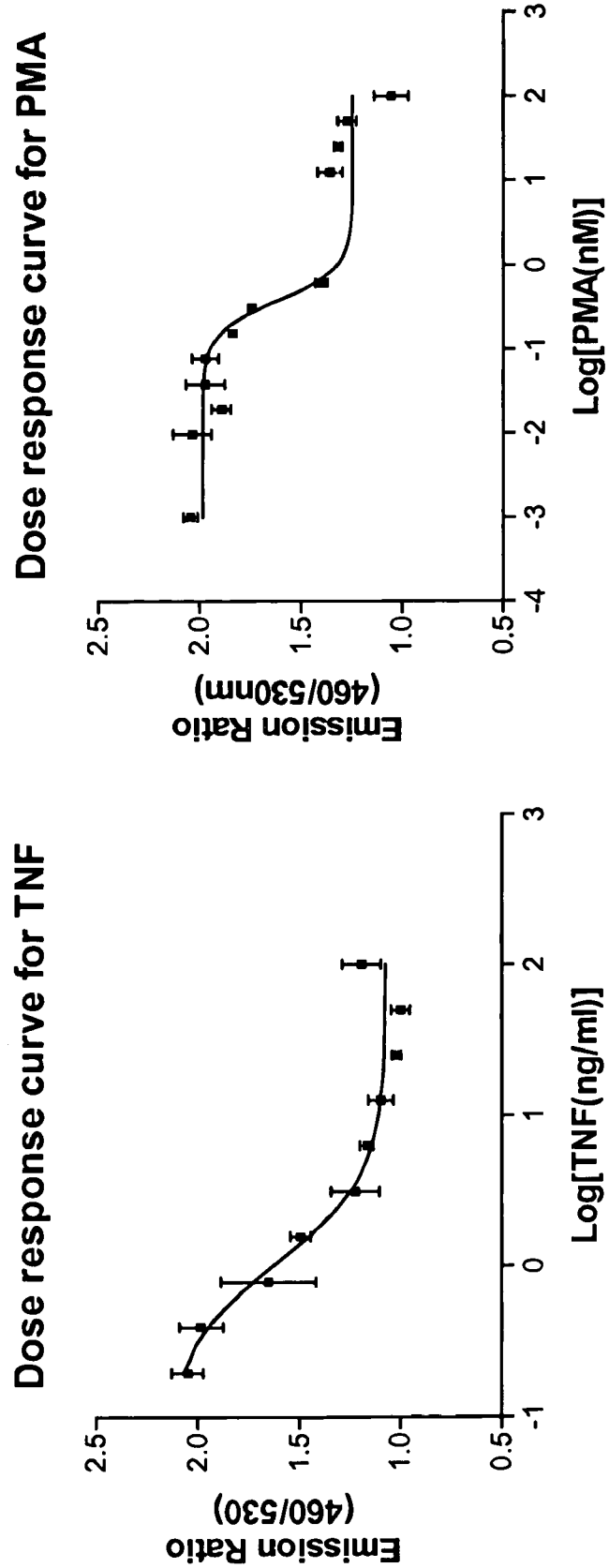
FIG. 8B shows the dose-response curves ($EC_{50}$ values) for TNFα and PMA.

Jurkat IκB-Bla cells were also used to determine $EC_{50}$ values for TNFα and PMA. Cells were treated with varying concentrations of TNFα for 1 hour at 37° C. or PMA for 4 hours at 37° C. The cells were then loaded with CCF2/AM and α-lactamase activity determined. FIG. 8B shows the dose-response curves for the two compounds. The $EC_{50}$ values are in the range that has been reported for other readouts such as the secretion of TNFα.

EXAMPLE 4

Responsiveness of Cells Transfected with Mutant Construct

Figure 9A:
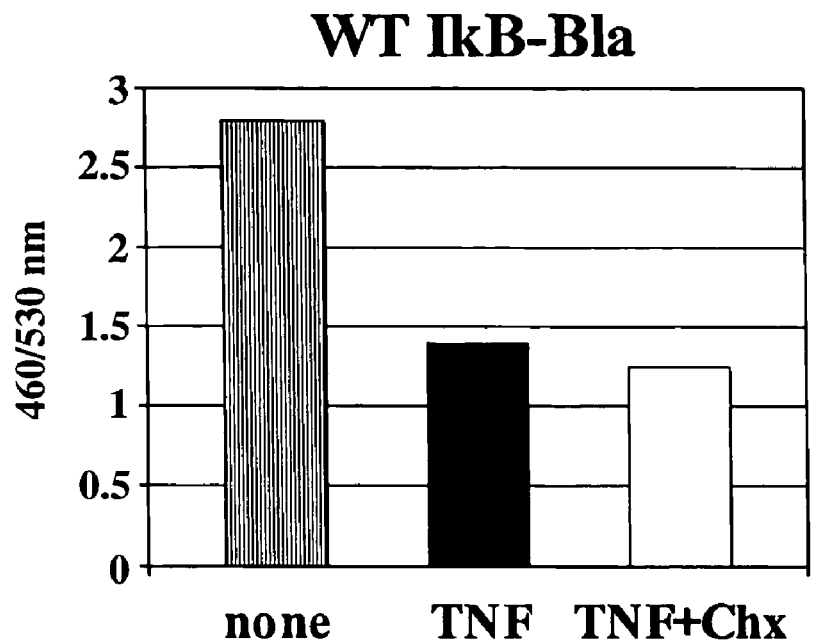
FIG. 9A shows the responsiveness of Jurkat cells expressing wild-type IκB-Bla construct to TNFα treatment.
Figure 9B:
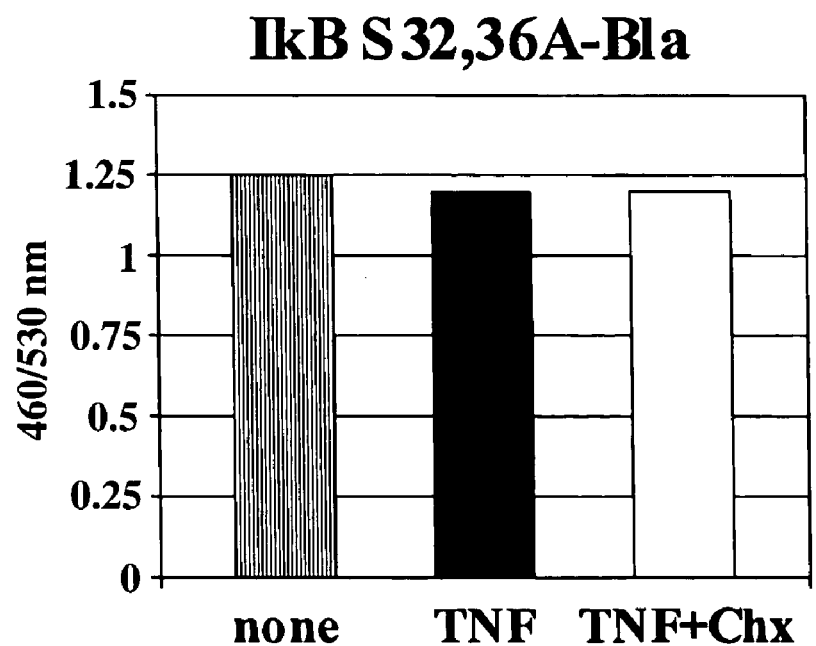
FIG. 9B shows the responsiveness of Jurkat cells expressing mutant (S32A, S36A) IκB-Bla construct to TNFα treatment.

To establish that the TNFα-stimulated decrease in β-lactamase activity was due to phosphorylation of IκB on serines-32 and -36, the responsiveness of Jurkat cells expressing the S32A, S36A IκB mutant as a fusion with β-lactamase was tested. The IκB(S32A, S36A)-Bla cell line was created exactly as described above for wild-type IκB-Bla cells. The cells were treated with 10 ng/ml TNFα for 30 minutes and then loaded with CCF2/AM. As shown in the comparison of wild-type construct to mutant in FIGS. 9A and 9B, respectively, the mutation of serines-32 and -36 abolished the decrease in β-lactamase activity in response to TNFα treatment. This experiment also showed that blocking protein synthesis by adding 100 μg/ml cycloheximide at the time of TNFα addition did not have a strong synergistic effect.

EXAMPLE 5

Dependence of β-Lactamase Activity on Proteasome Activity

The degradation of IκB has been shown to occur via the ubiquitin-proteasome pathway. Therefore, the requirement of proteasome activity on β-lactamase activity was tested. To accomplish this, Jurkat IκB-Bla cells were incubated in the presence of the proteasome inhibitor MG132 at 10 μM for 60 minutes prior to stimulating with TNFα to 10 ng/ml. Reporter activity was determined using CCF2/AM.

Figure 10:
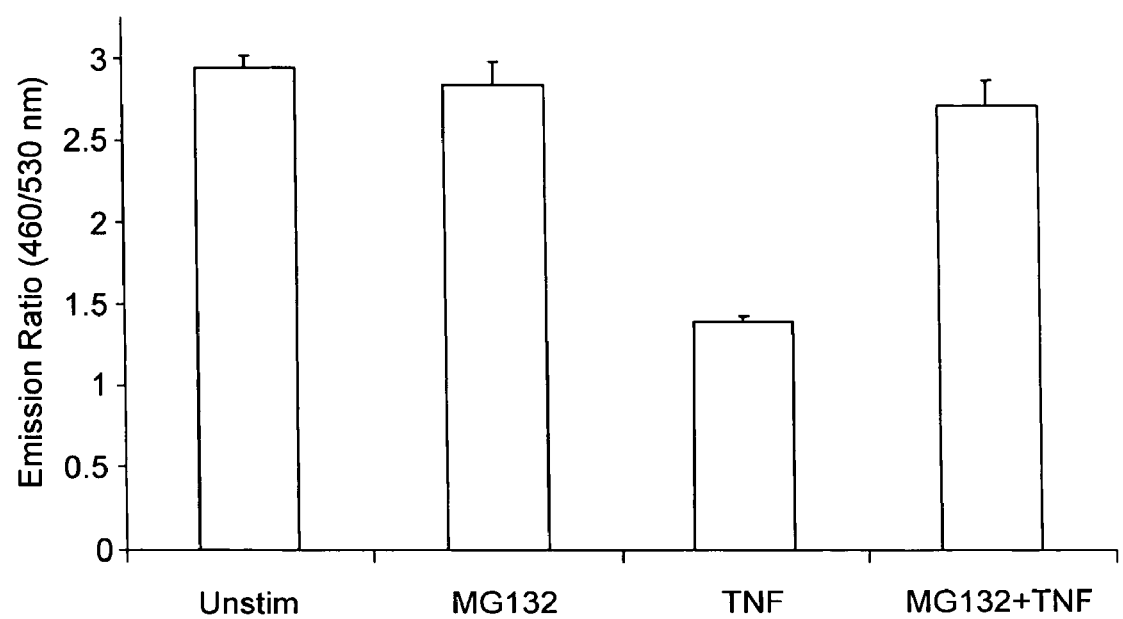
FIG. 10 shows the effect of the proteasome inhibitor MG132 on reporter levels.

As shown in FIG. 10, while MG132 alone had little to no effect on reporter levels, it efficiently inhibited the TNFα-stimulated decrease in reporter level. The $IC_{50}$ for two peptide inhibitors of the proteasome was also determined and it was found that they inhibited the TNFα-stimulated decrease in reporter levels with $IC_{50}$ values similar to that reported using model substrates for proteasome activity ($IC_{50}$ for MG132=2.3 μM and 5.0 μM for ALLN; data not shown).

EXAMPLE 6

Correlation of Reporter Levels with β-Lactamase Activity

The previous Examples establish that the β-lactamase readout in the IκB-Bla cells has the response characteristics and pharmacology necessary for a reporter of IKK activity. It was further desired to verify that the actual steady state levels of the reporter correlate with β-lactamase activity. To accomplish this, the physical levels of both the IκB-Bla reporter and IκB were determined by western blot and correlated these with the measurements of β-lactamase activity using CCF4 cleavage.

Figure 11A:
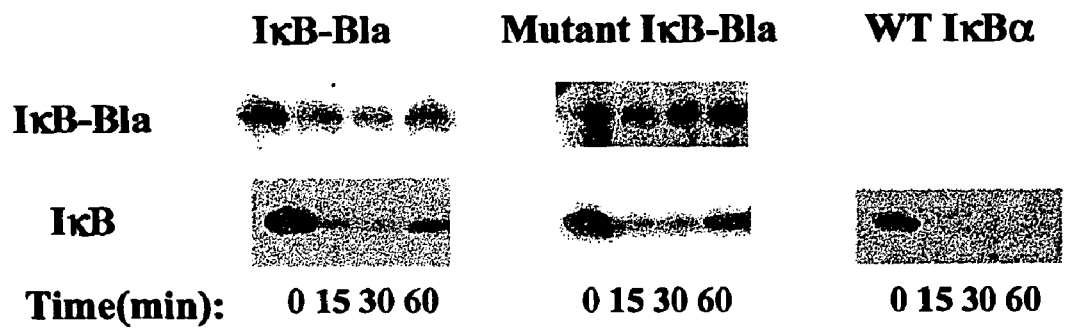
FIG. 11A is a western blot showing the results of treating wild type IκB-Bla or mutant (S32A, S36A) IκB-Bla cells with TNFα for 0, 15, 30 and 60 minutes.
Figure 11B:
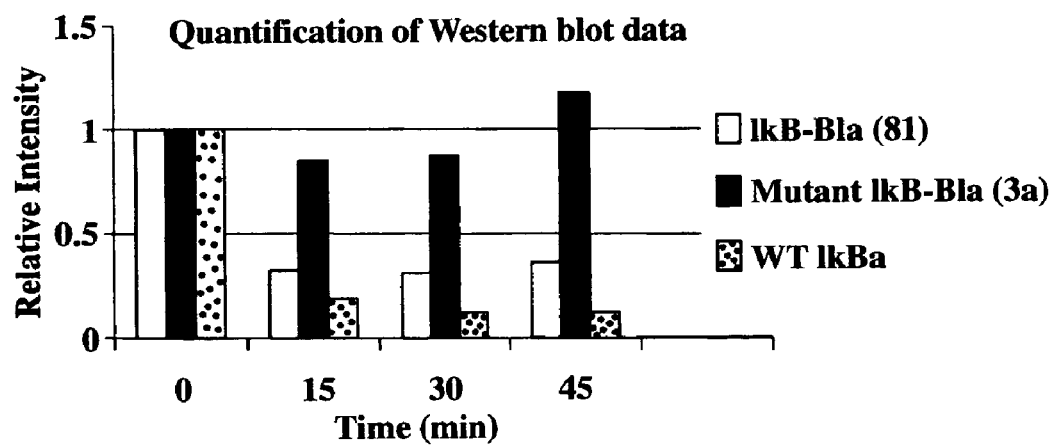
FIG. 11B shows the quantification of the western blot data shown in FIG. 11A.
Figure 11C:
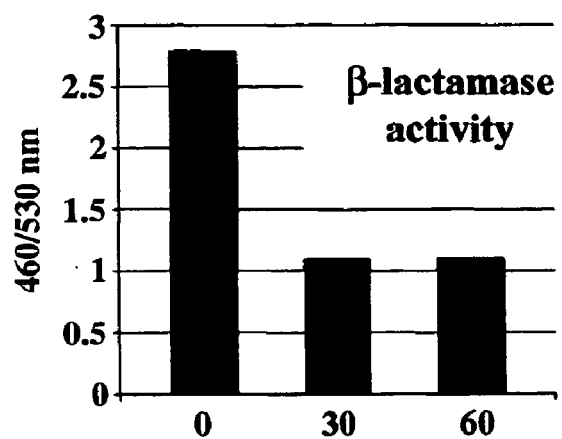
FIG. 11C shows β-lactamase activity for IκB-Bla cells treated with TNFα for 30 and 60 minutes by loading the cells with CCF4/AM and analysis by fluorescence plate reader.

FIG. 11A shows the results of treating IκB-Bla or IκB (S32A, S36A)-Bla cells with 10 ng/ml TNFα for 0, 15, 30 and 60 minutes and analyzing IκB and IκB-Bla levels by western blot. The resulting blots were probed with antisera specific for IκB. Detection was by ECL using HRP-conjugated secondary antibodies. The resulting autoradiograms from ECL detection were scanned by laser densitometry and protein levels were normalized relative to the zero minute time point (FIG. 11B). For comparison, β-lactamase activity was determined for IκB-Bla cells treated with 10 ng/ml TNFα for 30 and 60 minutes by loading the cells with CCF4/AM and analysis by fluorescence plate reader (FIG. 11C).

These analyses show that the decrease in β-lactamase levels seen in TNFα-treated IκB-Bla Jurkat cells correlates very well with the decrease in steady state levels of the IκB-Bla reporter protein as well as endogenous IκB. In addition, the western blot analysis confirm the lack of degradation of the IκB(S32A, S36A)-Bla control reporter under conditions where endogenous IκB is rapidly degraded. These results establish that the IκB-Bla reporter system is an accurate and reliable assay for the TNFα-signaled, IKK-mediated degradation of IκB.

EXAMPLE 7

IKK Inhibition

Figure 12:
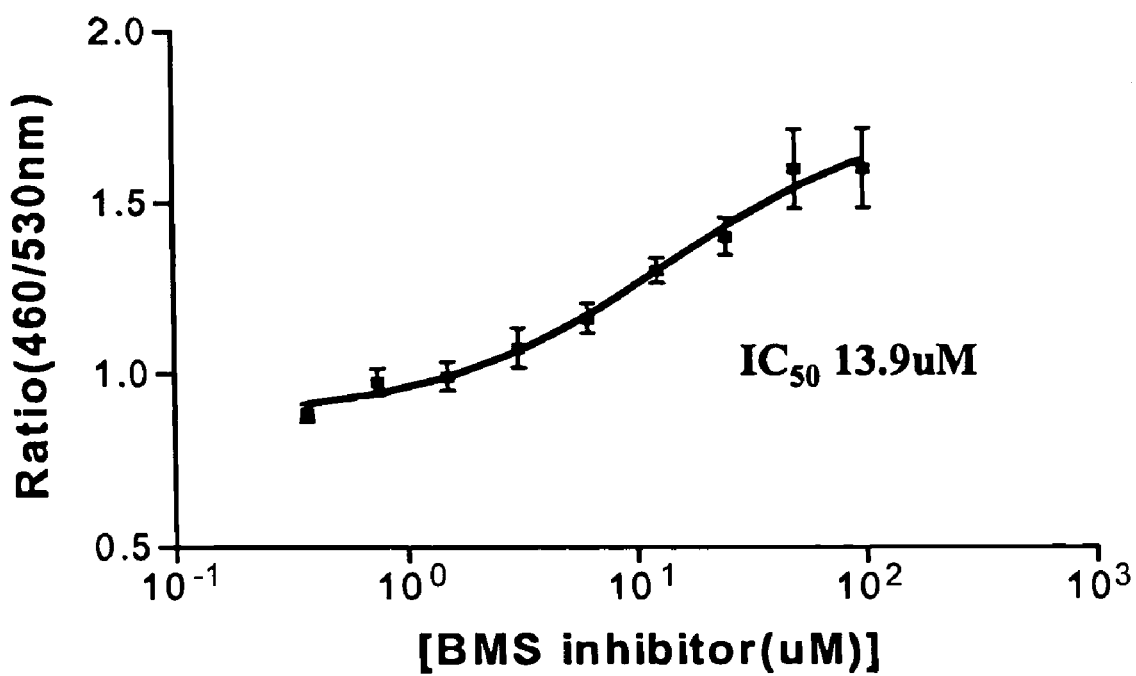
FIG. 12 shows the results of a dose-response experiment performed with an inhibitor of IKK.

An inhibitor of IKK, referred to as BMS-345541 (Burke et al., *The Journal of Biological Chemistry* (2003) 278:3, p. 1450-1456, hereby incorporated by reference in its entirety), was used to test the IκB-Bla Jurkat cell line. FIG. 12 shows the results of a dose-response experiment performed with this inhibitor using the β-lactamase readout from the IκB-Bla reporter. The cells were treated with varying concentrations of the inhibitor and then stimulated with 10 ng/ml TNFα for 30 minutes at 37° C. The cells were then loaded with CCF4/AM and β-lactamase activity determined using a fluorescence plate reader. The $IC_{50}$ of this inhibitor was found to be approximately 14 μM in several experiments.

The following Examples show the optimization of several experimental parameters and validation experiments that measure the performance of an assay of the present invention under screening conditions. The data in these Examples serve as a guide in determining the actual conditions under which assays of the present invention are performed.

EXAMPLE 8

Optimization of Serum Levels

Figure 13:
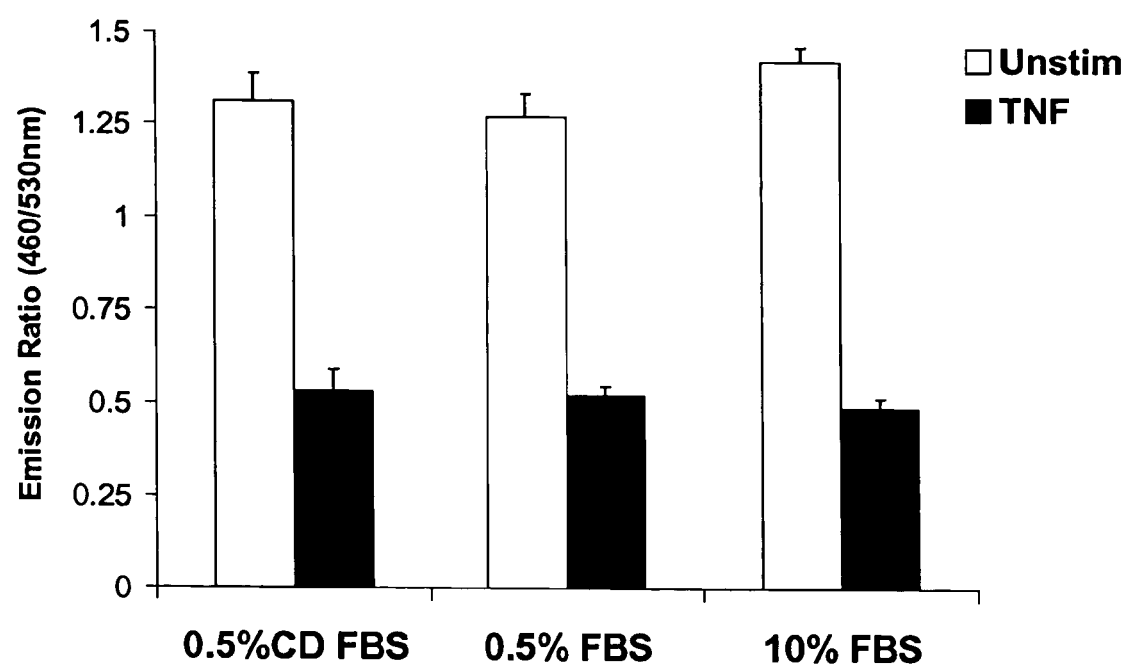
FIG. 13 shows the effects that reducing serum concentrations has on an assay of the present invention.

In order to determine optimal serum levels for use in the present invention, IκB-Bla Jurkat cells were cultured overnight in RPMI media supplemented with the indicated serum. The following morning, the cells were suspended in fresh media containing the indicated serum, treated with 10 ng/ml TNFα for 30 minutes and β-lactamase activity determined using CCF2/AM. In particular, fetal bovine serum (FBS) is a costly reagent as well as a source of possibly interfering growth factors. Therefore, the effect that reducing the concentration of FBS has on the performance of an assay of the present invention was determined. Charcoal dextran (CD)-treated serum was also tested, which is known to contain reduced levels of growth factors and related molecules. FIG. 13 shows that the serum concentration can be reduced to as low as 0.5% without seriously compromising the performance of assays of the present invention. Using CD-treated serum also had little effect on the assay, suggesting that factors in the serum are not likely to be a significant source of background signal.

EXAMPLE 9

Optimization of CCF4/AM Concentration and Loading Time

The concentration and loading time of the β-lactamase substrate CCF4/AM was also optimized for the inventive assay. CCF4/AM, rather than CCF2/AM, was used because it has a greater linear range for β-lactamase activity due to its slower hydrolysis and increased solubility in aqueous solutions (such as cell culture growth media).

Figure 14A:
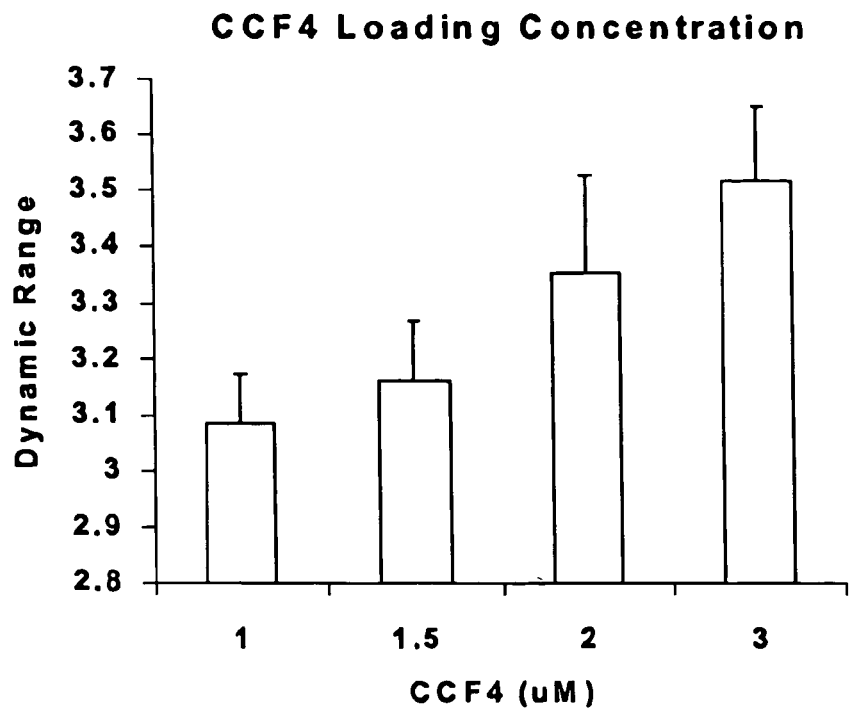
FIG. 14A shows the effect of increasing CCF4/AM concentration on the performance of any assay of the present invention.
Figure 14A:
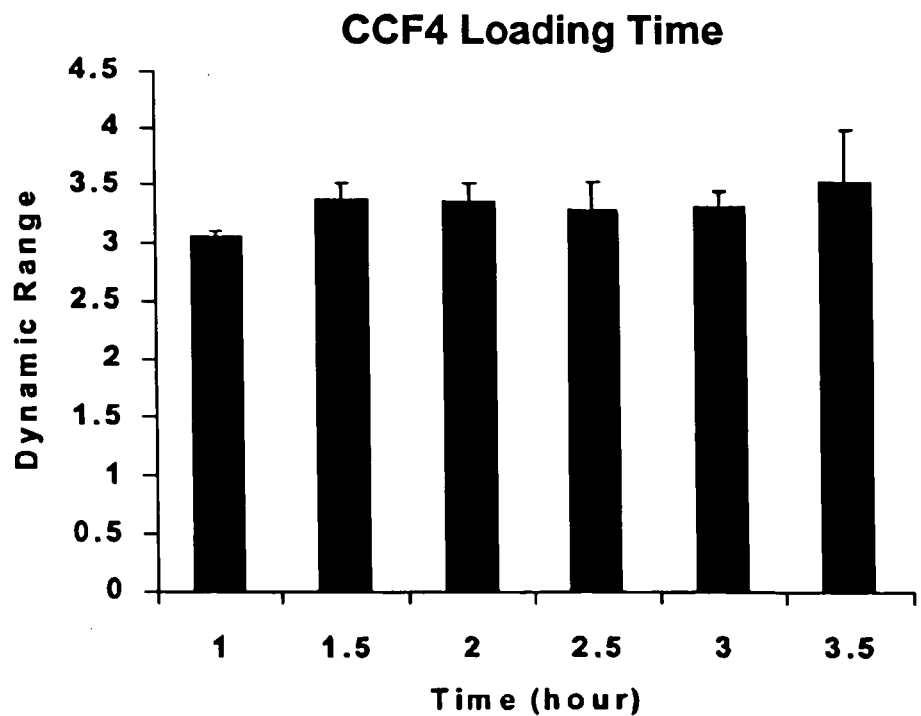

IκB-Bla Jurkat cells were treated with 10 ng/ml TNFα for 60 minutes, loaded with the indicated concentration of CCF4/AM for 2 hours at room temperature then read in a fluorescence plate reader. FIG. 14A shows that increasing the CCF4/AM concentration leads to an increase in assay dynamic range in general. A practical compromise between the cost of reagents and assay performance suggests that 1.5-2 μM CCF4/AM represent suitable concentrations of dye for screening applications.

The time of CCF4/AM loading experiment involved treatment with 10 ng/ml TNFα for 60 minutes then loading with 3 μM CCF4/AM for the indicated times before reading. FIG. 14B shows that CCF4/AM loading times from 1.5 to 3.5 hours at room temperature are appropriate.

EXAMPLE 10

Figure 15:
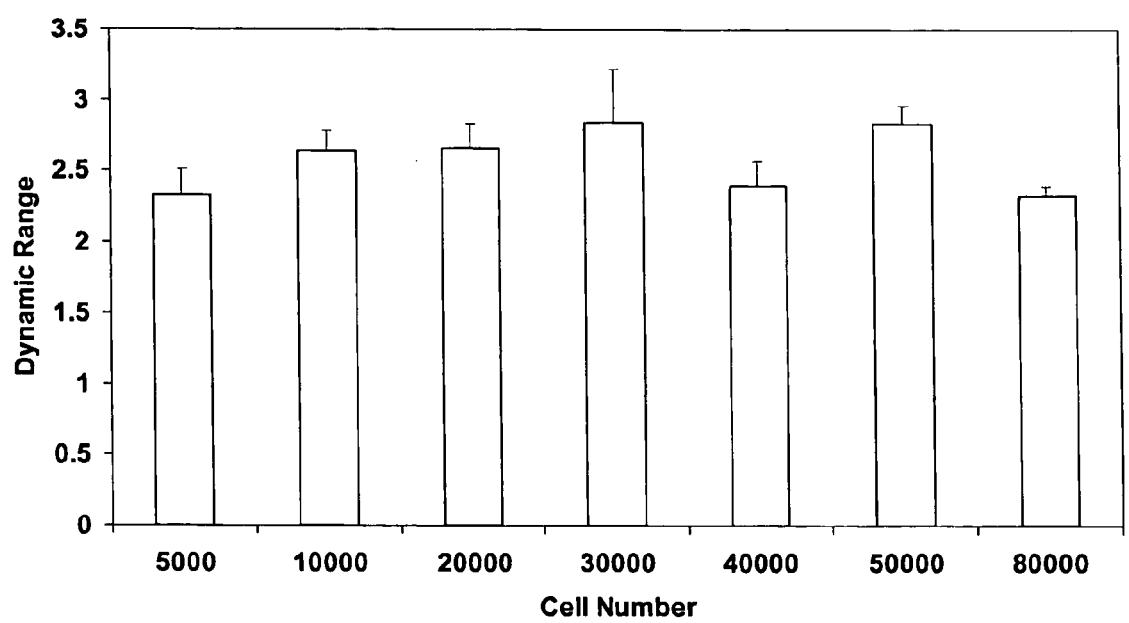
FIG. 15 shows the optimization of an assay of the present invention for cell number per well using TNFα stimulation of IκB-Bla Jurkat cells.

Optimization of Cell Number Per Well in a 384-Well Plate Using TNFα Stimulation of IκB-Bla Jurkat Cells Data in the present invention was generated using a 384-well format and an LJL Analyst fluorescence plate reader. FIG. 15 shows the optimization of an assay of the present invention for cell number per well using TNFα stimulation of IκB-Bla Jurkat cells. These data suggest that 10,000 to 30,000 cells per well are suitable for assays of the present invention.

EXAMPLE 11

Determination of DMSO Sensitivity

Figure 16:
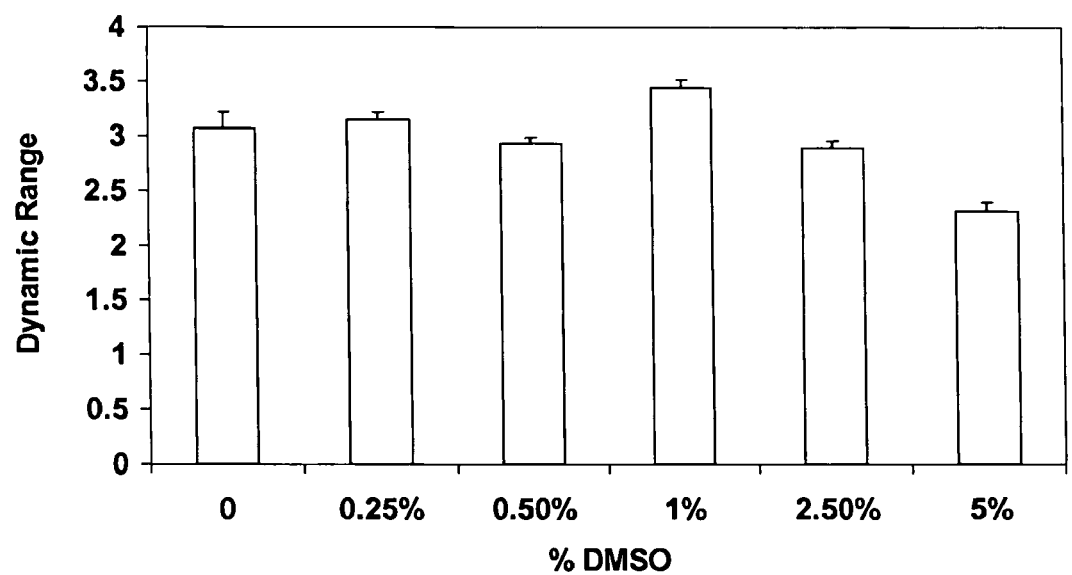
FIG. 16 shows the sensitivity of an assay of the present invention to DMSO.

The sensitivity of an assay of the present invention to DMSO was also determined. Jurkat IκB-Bla cells were treated with the indicated concentration of DMSO for 30 minutes prior to stimulation with TNFα. Consistent with other cell-based β-lactamase assays, assays of the present invention are tolerant to DMSO levels up to 1% with a decrease in assay performance at higher concentrations (FIG. 16).

EXAMPLE 12

Optimization of Time of Stimulation with TNFα

Figure 17:
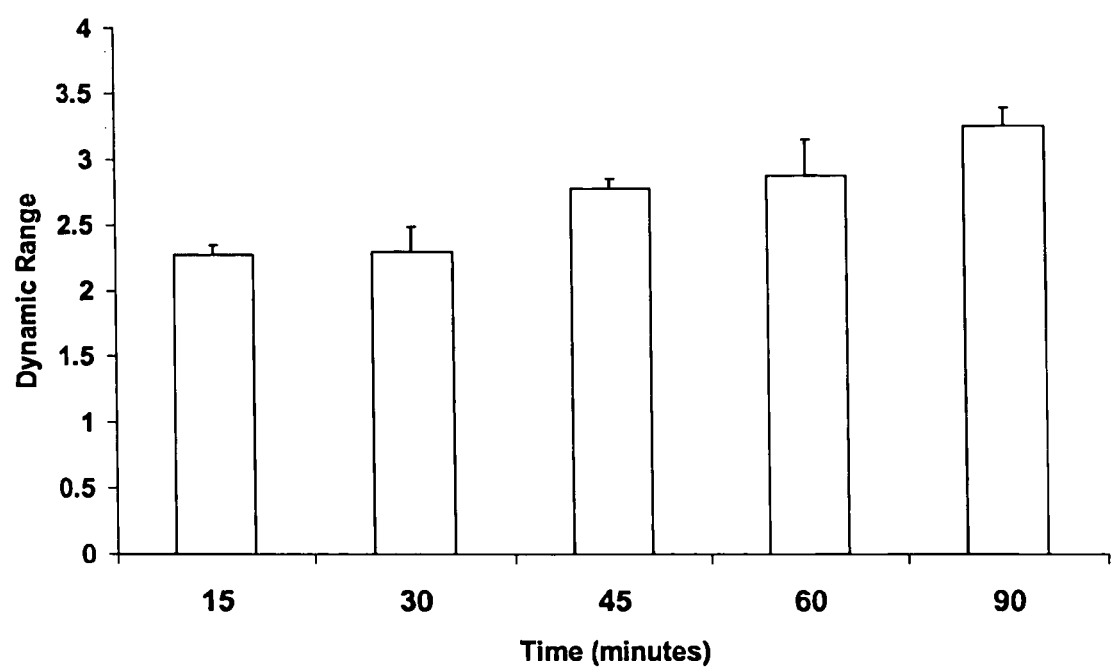
FIG. 17 shows the optimal time of stimulation of IκB-Bla Jurkat cells with TNFα.

The optimal time of stimulation with TNFα was also determined, as shown in FIG. 17. IκB-Bla Jurkat cells were treated with 10 ng/ml TNFα for the indicated time after which β-lactamase activity was determined using CCF4/AM. It is desired to use stimulation times of 45-60 minutes as longer times sometimes resulted in lower dynamic range due to increase in reporter levels, possibly as a result of desensitization of the cells to cytokine treatment (data not shown).

EXAMPLE 13

Assay Statistics

The calculation of the screening window parameter (1-Z') incorporates both dynamic range and reproducibility measurements. The screening window value for assays of the present invention was calculated using an experiment containing sixty wells per treatment (+/−10 ng/ml TNFα). The dynamic range of the assay in this experiment was 2.7-fold. The screening window calculated from this experiment was 0.205, indicating the high degree of reproducibility of the assay.

$$\frac{3(SD_T) + 3(SD_B)}{X_T - X_B} \leq 0.5$$

$$\frac{3(SD_T) + 3(SD_B)}{X_T - X_B} \leq 0.5$$

Where:
$SD_B$ is the standard deviation of the basal activity
$SD_T$ is the standard deviation of the maximal activity
$X_B$ is the mean basal activity, and
$X_T$ is the mean maximal activity Included is an analysis of well-to-well variability across an entire 384-well plate using the "checkerboard" pattern of alternating stimulated and unstimulated samples shown in FIG. 18. Table 2 below shows the assay statistics for three checkerboard-type experiments performed on three successive days.

TABLE 2

Assay Statistics for Well-to-Well Variability.

| Exp. | Emission ratio, no TNF | Std. Dev. | Emission ratio, 10 ng/ml TNF | Std. Dev. | Dynamic range | Screening window (1-z') |
|---|---|---|---|---|---|---|
| 1 | 1.96 | 0.149 | 0.686 | 0.0506 | 2.86 | 0.471 |
| 2 | 1.898 | 0.122 | 0.694 | 0.0717 | 2.73 | 0.483 |
| 3 | 1.752 | 0.0802 | 0.699 | 0.0415 | 2.51 | 0.347 |

The Examples and discussion above demonstrate that the β-lactamase readout of Jurkat IκB-Bla cells accurately reproduces the response of cells to proinflammatory cytokines like TNFα. In particular, assays of the present invention are shown to provide appropriate readout for IKK activity, which is known to lead to IκB degradation and NF-κB activation. Accordingly, the present invention provides a cell-based screening assay for IκB degradation occurring as a result of IκB kinase (IKK) activity.

The inventive assay utilizes Jurkat cells expressing a IκBα-β-lactamase fusion protein (IκB-Bla) to monitor the degradation kinetics of IκB upon stimulation of the NF-κB signaling pathway. β-lactamase activity rapidly decreases upon TNFα or PMA treatment and mirrors the decrease in IκB. The degradation of the IκB-Bla fusion protein is blocked by mutations altering the residues in IκB that are phosphorylated by IKK. The assay exhibits proper pharmacology as IκB-Bla degradation is efficiently blocked by inhibitors of the proteasome as well as an inhibitor of IKK. Further, the inventive assay has been optimized and fully validated in 384-well format.

As IKK-mediated phosphorylation of IκB is required for and followed by ubiquitination of IκB, which is required for and followed by proteasome-dependent degradation of IκB, assays and cell lines of the present invention are also useful for the study and characterization of proteasome and ubiquitin ligase inhibitors. The therapeutic utility of inhibitors of ubiquitin ligase is expected to be the same as that of IKK inhibitors. Proteasome inhibitors are expected to be useful in the treatment of cancer.

While the invention has been described in connection with specific embodiments therefore, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. All references cited herein are expressly incorporated in their entirety.

What is claimed is:

1. An assay for identifying a compound that inhibits IκB kinase (IKK) activity, comprising the steps of: (a) providing a cell which expresses an a fusion protein comprising SEQ ID NO: 2 (b) contacting said cell with a test compound; and (c) determining whether said test compound inhibits IKK activity.

2. An assay of claim 1, wherein said assay is a cell-based assay.

3. An assay of claim 1, wherein said assay is conducted in a high throughput manner.

4. An assay of claim 1, wherein said cell has ATTC Deposit Number PTA-4852.

5. An assay of claim 1, wherein said fusion protein is encoded by a nucleic acid molecule comprising the nucleic acid sequence set forth in SEQ ID NO:1.

6. An assay of claim 1, wherein said step of determining whether said test compound inhibits IKK activity is determined by measuring the expression of beta-lactamase.

* * * * *

SEQUENCE LISTING

```
<160> NUMBER OF SEQ ID NOS: 2

<210> SEQ ID NO 1
<211> LENGTH: 1752
<212> TYPE: DNA
<213> ORGANISM: Artificial
<220> FEATURE:
<223> OTHER INFORMATION: Artificial=Synthetic

<400> SEQUENCE: 1
atgttccagg cggccgagcg cccccaggag tgggccatgg agggcccccg cgacgggctg      60
aagaaggagc ggctactgga cgaccgccac gacagcggcc tggactccat gaaagacgag     120
gagtacgagc agatggtcaa ggagctgcag gagatccgcc tcgagccgca ggaggtgccg     180
cgcggctcgg agccctggaa gcagcagctc accgaggacg gggactcgtt cctgcacttg     240
gccatcatcc atgaagaaaa ggcactgacc atggaagtga tccgccaggt gaagggagac     300
ctggctttcc tcaacttcca gaacaacctg cagcagactc cactccactt ggctgtgatc     360
accaaccagc cagaaattgc tgaggcactt ctgggagctg gctgtgatcc tgagctccga     420
gactttcgag gaaataccc cctacacctt gcctgtgagc agggctgcct ggccagcgtg     480
ggagtcctga ctcagtcctg caccaccccg cacctccact ccatcctgaa ggctaccaac     540
```

-continued

```
tacaatggcc acacgtgtct acacttagcc tctatccatg gctacctggg catcgtggag    600
cttttggtgt ccttgggtgc tgatgtcaat gctcaggagc cctgtaatgg ccggactgcc    660
cttcacctcg cagtggacct gcaaaatcct gacctggtgt cactcctgtt gaagtgtggg    720
gctgatgtca acagagttac ctaccagggc tattctccct accagctcac ctggggccgc    780
ccaagcaccc ggatacagca gcagctgggc cagctgacac tagaaaacct tcagatgctg    840
ccagagagtg aggatgagga gagctatgac acagagtcag agttcacgga gttcacagag    900
gacgagctgc cctatgatga ctgtgtgttt ggaggccagc gtctgacgtt aggatccatc    960
atggacccag aaacgctggt gaaagtaaaa gatgctgaag atcagttggg tgcacgagtg   1020
ggttacatcg aactggatct caacagcggt aagatccttg agattttcg ccccgaagaa   1080
cgttttccaa tgatgagcac ttttaaagtt ctgctatgtg cgcggtatt atcccgtatt   1140
gacgccgggc aagagcaact cggtcgccgc atacactatt ctcagaatga cttggttgag   1200
tactcaccag tcacagaaaa gcatcttacg gatggcatga cagtaagaga attatgcagt   1260
gctgccataa ccatgagtga taacactgcg gccaacttac ttctgacaac gatcggagga   1320
ccgaaggagc taaccgcttt tttgcacaac atgggggatc atgtaactcg ccttgatcgt   1380
tgggaaccgg agctgaatga agccatacca acgacgagc gtgacaccac gatgcctgta   1440
gcaatggcaa caacgttgcg caaactatta actggcgaac tacttactct agcttcccgg   1500
caacaattaa tagactggat ggaggcggat aaagttgcag gaccacttct gcgctcggcc   1560
cttccggctg gctggttttat tgctgataaa tctggagccg gtgagcgtgg gtctcgcggt   1620
atcattgcag cactggggcc agatggtaag ccctcccgta tcgtagttat ctacacgacg   1680
gggagtcagg caactatgga tgaacgaaat agacagatcg ctgagatagg tgcctcactg   1740
attaagcatt gg                                                       1752
```

<210> SEQ ID NO 2
<211> LENGTH: 584
<212> TYPE: PRT
<213> ORGANISM: Artificial
<220> FEATURE:
<223> OTHER INFORMATION: Artificial=Synthetic

<400> SEQUENCE: 2

```
Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140
```

-continued

```
Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
                260                 265                 270

Thr Leu Glu Asn Leu Gln Met Leu Pro Glu Ser Glu Asp Glu Glu Ser
            275                 280                 285

Tyr Asp Thr Glu Ser Glu Phe Thr Glu Phe Thr Glu Asp Glu Leu Pro
290                 295                 300

Tyr Asp Asp Cys Val Phe Gly Gly Gln Arg Leu Thr Leu Gly Ser Ile
305                 310                 315                 320

Met Asp Pro Glu Thr Leu Val Lys Val Lys Asp Ala Glu Asp Gln Leu
                325                 330                 335

Gly Ala Arg Val Gly Tyr Ile Glu Leu Asp Leu Asn Ser Gly Lys Ile
                340                 345                 350

Leu Glu Ser Phe Arg Pro Glu Glu Arg Phe Pro Met Met Ser Thr Phe
            355                 360                 365

Lys Val Leu Leu Cys Gly Ala Val Leu Ser Arg Ile Asp Ala Gly Gln
    370                 375                 380

Glu Gln Leu Gly Arg Arg Ile His Tyr Ser Gln Asn Asp Leu Val Glu
385                 390                 395                 400

Tyr Ser Pro Val Thr Glu Lys His Leu Thr Asp Gly Met Thr Val Arg
                405                 410                 415

Glu Leu Cys Ser Ala Ala Ile Thr Met Ser Asp Asn Thr Ala Ala Asn
            420                 425                 430

Leu Leu Leu Thr Thr Ile Gly Gly Pro Lys Glu Leu Thr Ala Phe Leu
        435                 440                 445

His Asn Met Gly Asp His Val Thr Arg Leu Asp Arg Trp Glu Pro Glu
    450                 455                 460

Leu Asn Glu Ala Ile Pro Asn Asp Glu Arg Asp Thr Thr Met Pro Val
465                 470                 475                 480

Ala Met Ala Thr Thr Leu Arg Lys Leu Leu Thr Gly Glu Leu Leu Thr
                485                 490                 495

Leu Ala Ser Arg Gln Gln Leu Ile Asp Trp Met Glu Ala Asp Lys Val
            500                 505                 510

Ala Gly Pro Leu Leu Arg Ser Ala Leu Pro Ala Gly Trp Phe Ile Ala
        515                 520                 525

Asp Lys Ser Gly Ala Gly Glu Arg Gly Ser Arg Gly Ile Ile Ala Ala
    530                 535                 540

Leu Gly Pro Asp Gly Lys Pro Ser Arg Ile Val Val Ile Tyr Thr Thr
545                 550                 555                 560
```

-continued

```
Gly Ser Gln Ala Thr Met Asp Glu Arg Asn Arg Gln Ile Ala Glu Ile
            565                 570                 575

Gly Ala Ser Leu Ile Lys His Trp
            580
```